United States Patent [19]

Stauffer

[11] Patent Number: 5,099,084

[45] Date of Patent: * Mar. 24, 1992

[54] PROCESS FOR THE CHLORINATION OF METHANE

[76] Inventor: John E. Stauffer, 6 Pecksland Rd., Greenwich, Conn. 06831

[*] Notice: The portion of the term of this patent subsequent to Feb. 6, 2007 has been disclaimed.

[21] Appl. No.: 297,298

[22] Filed: Jan. 13, 1989

Related U.S. Application Data

[63] Continuation-in-part of Ser. No. 40,839, Apr. 20, 1987, abandoned, which is a continuation-in-part of Ser. No. 793,534, Oct. 31, 1985, abandoned.

[51] Int. Cl.$^5$ .................... C07C 17/10; C07C 17/158
[52] U.S. Cl. .................... 570/241; 570/261; 570/244
[58] Field of Search .................... 570/241, 261

[56] References Cited

U.S. PATENT DOCUMENTS

| | | | |
|---|---|---|---|
| 2,447,410 | 8/1948 | Hampel | 570/220 |
| 2,547,139 | 4/1951 | Randall | 260/660 |
| 3,420,901 | 1/1969 | Schulz | 570/243 |
| 3,642,918 | 2/1972 | Bohl et al. | 570/224 |
| 4,192,822 | 3/1980 | Sweeney et al. | 570/261 |

Primary Examiner—J. E. Evans
Attorney, Agent, or Firm—Krass & Young

[57] ABSTRACT

A process is provided for the chlorination of methane using hydrogen chloride as a source of chlorine. The process includes reaction steps operated in tandem in separate zones first comprising the reaction of perchloroethylene with hydrogen chloride and oxygen in the presence of an oxychlorination catalyst to give hexachloroethane and water, and second comprising the vapor phase reaction of hexachloroethane with methane feedstock to produce chlorinated methane, perchloroethylene and hydrogen chloride.

8 Claims, 1 Drawing Sheet

PROCESS FOR THE CHLORINATION OF METHANE

REFERENCE TO A RELATED APPLICATION

This application is a continuation-in-part of copending application Ser. No. 040,839 filed Apr. 20, 1987, now abandoned, which in turn is a continuation-in-part of copending application Ser. No. 793,534, filed Oct. 31, 1985, now abandoned.

FIELD OF THE INVENTION

This invention relates to a novel method of chlorinating methane comprising two reaction steps operated in tandem: oxychlorination of perchloroethylene ($CCl_2CCl_2$) to obtain hexachloroethane ($CCl_3$—$CCl_3$) and reaction of the latter as the chlorinating agent with methane to obtain methyl chloride ($CH_3Cl$), and by recycling, the partially and fully chlorinated methanes, methylene chloride ($CH_2Cl_2$), chloroform ($CHCl_3$) and carbon tetrachloride ($CCl_4$). The process has the distinct advantage of providing high yields and minimizing the production of unwanted by-products. The process thus offers significant cost savings over existing technology.

BACKGROUND OF THE INVENTION

Description of the Prior Art

The conventional method of producing chlorinated methanes involves the reaction of methane with chlorine gas. For each substitution of a chlorine atom into the methane molecule, one molecule of hydrogen chloride is produced. Thus, double the amount of chlorine is consumed compared with the quantity incorporated into the desired chlorinated hydrocarbon. In other words, the maximum chlorine efficiency is 50 percent. Since the cost of chlorine is a major factor in the cost of producing chlorinated methanes, any inefficiency in its use is a severe handicap.

Alternative chlorination methods have been tried over the years with varying success. The object of these methods has been to produce chlorinated methanes without the coproduction of hydrogen chloride. For example, by starting with methyl alcohol (methanol) and hydrogen chloride, methyl chloride can be produced. This produce is useful by itself, or in turn it can be reacted with chlorine to give methylene chloride and hydrogen chloride. Since the latter can be recycled to the methanol reaction step, the net production of hydrogen chloride is zero.

While the above scheme, which starts with methanol, is used commercially, it nevertheless has certain drawbacks. To begin with, methanol is more expensive than methane from which it is produced. Furthermore, only methyl chloride or methylene chloride can be made in balanced reactions. If the more highly chlorinated methane products, namely, chloroform or carbon tetrachloride are desired, excess hydrogen chloride must be disposed of.

In order to circumvent the shortcomings of existing technology, numerous attempts have been made to oxychlorinate methane. Methods, for example, employing oxyhalogenation and related technology are described in U.S. Pat. Nos. 3,470,260, 2,334,033, 2,498,546, 3,173,962, 3,345,422, 4,000,205, 4,020,117, 4,284,833, 4,386,28, and 4,446,249.

Although oxychlorination appears in theory to offer advantages, there are many technical difficulties with the process. For example, at sufficiently high temperatures which are required for chlorination, some of the methane begins to burn with the air. Such combustion may lead to the formation of hot spots in the catalyst bed thereby complicating the problem of temperature control. With overheating, the catalyst may gradually lost its efficiency. Also, whatever hydrocarbon is burned reduces the yield of product. Finally, there is the ever present danger of explosions should, for one reason or another, the supply of hydrogen chloride to the reactor be interrupted.

It is therefore an object of the present invention to provide a method for the chlorination of methane that overcomes the disadvantages of the conventional methods.

It is also an object to provide a method of the kind described with includes endothermic and exothermic reactions, namely substitution chlorination and dissociation, that are carried out in tandem such that the overall energy requirements can be closely balanced.

These and other objects, features and advantages of the invention will be apparent from the following description and the accompanying drawing in which:

SUMMARY AND DETAILED DESCRIPTION

Figure 1:
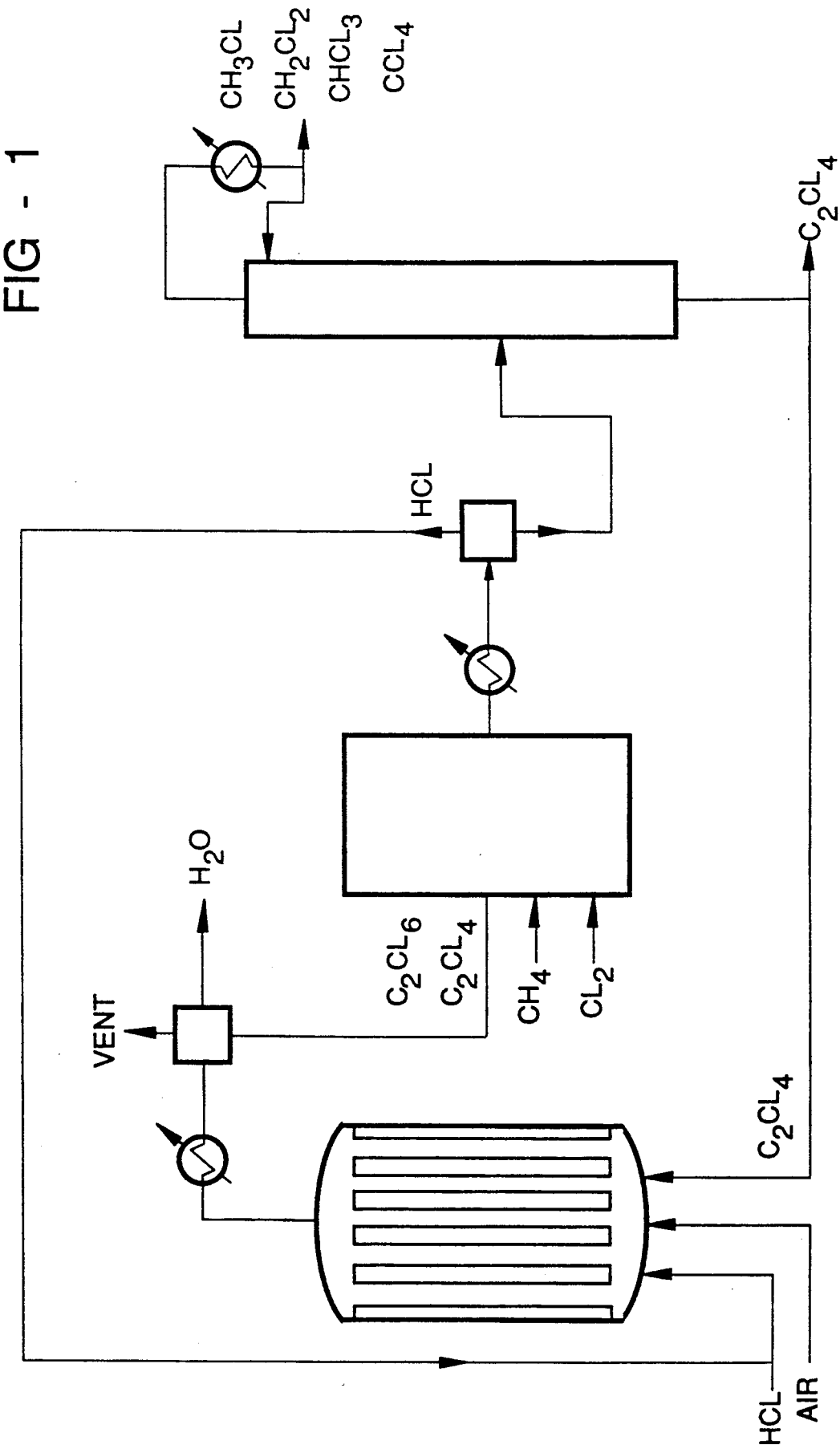
FIG. 1 is a diagrammatic representation of preferred means for operating the present chlorination method including a shell and tube catalytic reactor in series with a thermal reactor with means for recycling and for withdrawal of chlorinated product and fractionation.

The invention in one preferred embodiment concerns a process for the chlorination of methane using hydrogen chloride as a source of chlorine. The process includes reaction steps operated in tandem in separate reaction zones first comprising the reaction of perchloroethylene with hydrogen chloride and oxygen in the presence of an oxychlorination catalyst to give hexachloroethane and water, and second comprising the vapor phase reaction of hexachloroethane with methane feedstock to produce chlorinated methane, perchloroethylene and hydrogen chloride.

The invention in another Preferred embodiment concerns a process for the chlorination of methane using hydrogen chloride as a source of chlorine, said process including reaction steps operated in tandem first subjecting perchloroethylene to oxychlorination with hydrogen chloride and oxygen in the presence of an oxychlorination catalyst to give reaction products consisting essentially of hexachloroethane and water; second, isolating said hexachloroethane from the reaction products and reacting it with methane feedstock in the vapor phase to produce products consisting essentially of chlorinated methane, perchloroethylene and hydrogen chloride; and third, isolating said products of the second step and repeating the first step using as starting materials the perchloroethylene and hydrogen chloride thus isolated whereby chlorination using regenerated hexachloroethane is accomplished, the process is operated with total utilization of hydrogen chloride, and net production of hydrogen chloride and hexachloroethane is avoided.

Problems encountered by the conventional methods are avoided by the method of the present invention. In the present method according to a preferred embodiment, two separate reactions are carried out in tandem, as indicated. First, perchloroethylene is reacted with hydrogen chloride and air or oxygen to produce hexachloroethane and water. In the second reaction the hexachloroethane is reacted with methane or methane feedstock (including chlorinated methane or a mixture of chlorinated methanes) to give the desired chlorinated hydrocarbon plus hydrogen chloride. The latter (hydrogen chloride) is recycled to the first reaction so that there is no net production of hydrogen chloride.

The reactions in the present invention are illustrated by the following equations for the preparation of methyl chloride:

$$CCl_2=CCl_2 + 2HCl + 1/2O_2 \xrightarrow{cat.} CCl_3CCl_3 + H_2O \qquad 1.$$

$$CCl_3CCl_3 + CH_4 \xrightarrow{\Delta} CCl_2=CCl_2 + CH_3Cl + HCl \qquad 2a.$$

Therefore the net reaction is:

$$CH_4 + HCl + \tfrac{1}{2}O_2 \rightarrow CH_3Cl + H_2O \qquad 3.$$

If, in preferred embodiment, chlorine is added in the second step, the following reaction will occur:

$$Cl_2 + CH_4 \rightarrow CH_3Cl + HCl$$

The first reaction, in which perchloroethylene is oxychlorinated to hexachloroethane employing an oxychlorination catalyst may typically be carried out in a molten salt reactor, fluidized bed reactor, or in a shell and tube reactor. The temperature is maintained Preferably in the range from about 200° to about 375° C. The catalyst of choice is copper chloride deposited on an inert support. This is the well-known Deacon catalyst which has been used in experimental processes to produce chlorine from hydrogen chloride and air. Various salts may be mixed with the copper chloride to promote its effectiveness, e.g., potassium chloride, ferric chloride, and lead chloride.

The second reaction is conducted in the vapor phase at an elevated temperature preferably in the range from about 400° to about 700° C. The probable mechanism by which methane is chlorinated is a series of free-radical reactions. In the event that insufficient hydrogen chloride is available to produce the required hexachloroethane, chlorine can be added to supplement the hexachloroethane. Thus, various predetermined proportions of hydrogen chloride and chlorine, depending on requirements, can be used in the overall process.

In preferred embodiments, by adjusting the conditions under which the second reaction is carried out, chlorinated methanes other than methyl chloride may be produced. Thus, two substitutions of chlorine into the methane molecule will give methylene chloride, three substitutions provide chloroform, and the complete replacement of hydrogen atoms by chlorine produces carbon tetrachloride. In addition, some perchloroethylene may be formed beyond what is produced from the decomposition of hexachloroethane. The mix of these products depends on such factors as the reaction temperature and the concentrations of the intermediates. For example, by recycling methyl chloride to the second reaction step, the net production of methyl chloride will be nil.

As a feature of the invention, temperature control of the second reaction is facilitated using hexachloroethane instead of chlorine as the chlorinating agent. Substitution chlorination such as the formation of methyl chloride from methane and chlorine releases considerable heat. By contrast, dissociation reactions such as the instant decomposition of hexachloroethane to perchloroethylene and chlorine absorb a substantial quantity of heat. Thus, according to the present invention, when these two reactions, substitution chlorination and dissociation, are conducted in an intimate manner, the heat requirements can be closely balanced.

Operation of the process is illustrated in the attached drawing. Air, hydrogen chloride and perchloroethylene are fed to the shell and tube reactor which contains the copper chloride catalyst. The effluent is cooled sufficiently to condense the liquids. The inert gases are vented to a scrubber while a separator decants the water from the chlorinated organics. Hexachloroethane dissolved in unreacted perchloroethylene is pumped to the thermal reactor where it chlorinates methane. The hot vapors from the reactor are cooled, the hydrogen chloride is separated for recycle to the catalytic reactor, and the chlorinated solvents are fractionated in a distillation column and the fractions recovered. The perchloroethylene still bottoms are returned to the oxychlorination step.

Although the process as described seems rather straightforward, successful operation depends on the strict adherence to the following rules:

1. Hexachloroethane produced via oxychlorination must be isolated from the reaction products before being fed to the thermal reactor. Any impurities, with the exception of perchloroethylene, must be separated from the hexachloroethane in order to avoid the formation of byproducts, which are difficult to separate and which reduce the hydrogen chloride efficiency. The thermal reactor must be kept under anhydrous conditions or above the dew point to prevent severe corrosion problems. All oxygen has to be excluded from the thermal reactor to avoid burning and to prevent the formation of water.

2. Hydrogen chloride, before being recycled to the oxychlorination reactor, must be freed of all hydrocarbons to prevent combustion reactions and to avoid pollution problems caused by the release of hydrocarbons in the vent gases.

3. Perchloroethylene that is reformed in the thermal reactor must be isolated from the product stream before being recycled to the oxychlorination reactor. Any saturated hydrocarbons which are fed to the oxychlorination reactor will be subject to burning. Unsaturated hydrocarbons, other than perchloroethylene, will be chlorinated in the oxychlorination reactor and eventually lead to unwanted byproducts. Any volatile impurities will escape in the vent gases.

The necessary separations of the recycle streams cannot be taken for granted. For example, hexachloroethane is very slightly miscible in water and thus presents a challenge in drying it completely. The principles of azeotropic distillation are used to separate hydrogen chloride. And finally, in isolating perchloroethylene from the product stream the differences in boiling points determine its ease of fractionation.

The chlorinated solvents produced by the method of the invention are valuable items of commerce. Methyl chloride is an intermediate for the production of silicones. Methylene chloride is used as a propellant in aerosols. It also is an effective paint remover. Both chloroform and carbon tetrachloride are consumed in large quantities in the production of fluorocarbons.

Perchloroethylene, which is non-flammable, is a safe and effective dry cleaning solvent.

The embodiments of the invention in which exclusive property or privilege is claimed are defined as follows:

1. A process for the chlorination of methane using hydrogen chloride as the source of chlorine and avoiding net production of hydrogen chloride, said process consisting essentially of steps operated in tandem:

first, subjecting chlorinated ethylene consisting essentially of perchloroethylene to oxychlorination with hydrogen chloride and oxygen in the presence of an oxychlorination catalyst to give reaction products consisting essentially of hexachloroethane and water;

second, isolating said hexachloroethane from the reaction products of the first step and reacting it with methane feedstock in the vapor phase to produce products consisting essentially of chlorinated methane, perchloroethylene, and hydrogen chloride; and third, isolating perchloroethylene and hydrogen chloride from hydrocarbon products of the second step and recycling the hydrogen chloride and perchloroethylene thus isolated to the first step whereby chlorination using regenerated hexachloroethane is accomplished, the process is operated with total utilization of hydrogen chloride, and net production of hydrogen chloride is avoided.

2. A process according to claim 1 in which elemental chlorine is added to the second step such that the second step comprises the reaction of chlorine and methane to produce chlorinated methanes and hydrogen chloride.

3. A process according to claim 1 in which partially chlorinated methanes produced in step 2 are recycled to step 2 for further chlorination.

4. A process according to claim 1 in which the methane feedstock to step 2 comprises a chlorinated methane or a mixture of chlorinated methanes.

5. A process according to claim 1 in which the catalyst used in step 1 comprises copper chloride on an inert support.

6. A process according to claim 5 where the catalyst comprises an admixture of copper chloride with a salt selected from the group consisting of potassium chloride, ferric chloride, and lead chloride.

7. A process according to claim 1 in which the oxychlorination reaction with perchloroethylene is carried at temperatures in the range from about 200° to about 375° C.

8. A process according to claim 1 in which the vapor phase reaction is carried out at temperatures in the range from about 400° to about 700° C.

* * * * *